US00PP10330P

United States Patent [19]

Sakazaki

[11] Patent Number: Plant 10,330

[45] Date of Patent: Apr. 14, 1998

[54] PETUNIA PLANT NAMED '(REVOLUTION VIOLET NO. 3)'

[75] Inventor: Ushio Sakazaki, Hikone, Japan

[73] Assignee: Suntory Limited, Osaka, Japan

[21] Appl. No.: 746,555

[22] Filed: Nov. 13, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,489 | 12/1993 | Hirabayashi et al. | Plt./68.1 |
| P.P. 8,768 | 6/1994 | Hirabayashi et al. | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,556 | 5/1996 | Tachibana et al. | Plt./68.1 |
| P.P. 9,557 | 5/1996 | Suzuki et al. | Plt./68.1 |

*Primary Examiner*—James R. Feyrer
*Assistant Examiner*—Elizabeth C. Kemmerer
*Attorney, Agent, or Firm*—Morgan & Finnegan; Eugene Moroz; Mary J. Morry

[57] ABSTRACT

Disclosed herein is a petunia plant, having a decumbent habit plant having long stems. The petunia plant has over-abundant branching, particularly primary branching is strong, and great profusion blooms, the whole bush remaining in bloom for a considerable period of time. The flowers are single and large, the petals having a vivid purple color, and the bottom color of the corolla throat is vivid purple and the outside of corolla tube is strong purple. The plant has a high resistance to rain, heat, drought and pest.

2 Drawing Sheets

BACKGROUND OF THE VARIETY

The present invention relates to a new and distinct variety of petunia plant obtained from crossing one petunia plant (♀) which was selected from a crossing of "Falcon Blue" (♀) and a wild type of petunia plant (♂) native to Brazil, and the other petunia plant (♂) which was selected from a crossing of "Falcon Blue" (♀) and a wild type of petunia plant (♂) native to Brazil.

The petunia is a very popular plant and is used for flower bedding and potting in the summer season. There are only a few varieties of the petunia plant which do not have an upright growth habit and which have a high resistance to rain, heat, cold, and diseases. The petunia which we previously filed, i.e., the "Revolution" series [(Revolution Purplepink(U.S. Plant Pat. No. 6,915), Revolution Brilliantpink (U.S. Plant Pat. No. 6,914), Revolution Brilliantpink-mini (U.S. Plant. Pat. No. 6,899)] is a decumbent type plant having long stems, a lower plant height, abundant branching, and a high resistance to heat, cold and rain. However, there are only a few varieties having a great profusion of flowers, pastel color flower petals and a high resistance to rain, heat, cold and diseases. Accordingly, this invention was aimed at obtaining a new variety having a vivid purple color petal, together with the above features.

The new variety of petunia plant according to this invention originated from crossing one petunia plant (♀) which was selected from a crossing of "Falcon Blue" (♀) and a wild type of petunia plant (♂) native to Brazil, and the other petunia plant (♂) which was selected from a crossing of "Falcon Blue" (♀) and a wild type of petunia plant (♂) native to Brazil.

First of all, 350 seedlings were obtained from crossing "Falcon Blue" as female parent and a wild type of petunia plant as pollen parent in June, 1991. From this crossing 2 seedlings were selected in view of decumbent habit and vivid purple flower color. And then 350 seedlings were obtained from a crossing of these selected 2 seedlings in March, 1992. These 350 seedlings were grown and 5 seedlings were selected from these. These selected 5 seedlings were carried out a trial by flower potting and bedding, and then the only one plant selected in March, 1993. The botanical characteristics of the finally-selected plant were then examined, using similar variety "Falcon Blue" for comparison, from March, 1993. As a result, it was concluded that this petunia is distinguishable from any other variety, whose existence is known to us, sufficiently uniform and stable in its characteristics, then this new variety of petunia plant was named "Revolution Violet No. 3".

In the following description, the color-coding is in accordance with The Horticultural Colour Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The female parent use in the crossing of two petunia plant which use in the crossing of "Revolution Violet No. 3" was a wild type of petunia native to Brazil, the seeds of which were gathered at Gramado, Rio Grande Do Sul, Brazil and introduced to Japan in October, 1983. This wild type of petunia plant is presently maintained at the Plant Biotechnology Laboratory of SUNTORY Ltd., residing at 863-1, Aza-Iketani, Oomori-cho, Youkaiti-shi, Shiga-ken, Japan. The main botanical characteristics of this female parent use in the crossing of two petunia plant which use in the crossing of "Revolution Violet No. 3" are as follows.

Plant:

*Growth habit.*—Decumbent.

*Plant height.*—20 cm.

*Spreading area of plant.*—100–150 cm in diameter.

*Blooming period.*—May to August in the southern Kanto area, Japan.

Stem:

*Extending (length from base.).*—50–80 cm.

*Thickness.*—Main stem 2.0–3.0 mm; lateral stem 1.5–2.5 mm.

*Pubescence.*—Many.
*Branching.*—Over-abundant.
*Length of internode.*—1.0–2.0 cm before blooming: 1.5–3.0 cm during blooming.
*Color*—Strong yellow green (R.H.S. 144B-144C. JHS 3512-3513).

Leaf:
*Shape.*—Oval.
*Length.*—4.5–5.5 cm.
*Width.*—2.5–3.5 cm.
*Color.*—Grayish olive green (R.H.S. 137A-137B. JHS 3716–3717)
*Phyllotaxis.*—Opposite both before and during blooming.
*Pubescence.*—Few.

Flower:
*Facing direction.*—Opening obliquely upward.
*Type.*—Single.
*Shape.*—Funnel-shape, with five-fissured limb.
*Diameter.*—4.0–5.0 cm.
*Color.*—In the unopened stage (bud), dark reddish purple (R.H.S. 79B, JHS 8907–8909); when open, vivid reddish purple (R.H.S. 74A, JHS 9207), at full bloom, vivid reddish purple (R.H.S. 80A, JHS 8906).
*Reproductive organs.*—1 normal pistil and 5 normal stamens.
*Peduncle.*—0.9–1-2 mm in thicknes, and 2.0–2.5 cm in length.

Physiological and ecological characteristics: High resistance to cold, relatively high resistance to heat, and moderate resistance to disease and pests.

"Falcon Blue", used as pollen parent in the crossing of two petunia plants in the crossing of "Revolution Violet No. 3", is one of the Falcon Series bred by the Sakata Seed Corp., Japan. The Falcon Series includes "Falcon Red Morn", "Falcon Rose", and "Falcon Red", and these plants are commonly characterized by their large flower size. The main botanical characteristics of "Falcon Blue" are as follows.

Plant:
*Growth habit.*—Medium upright.
*Plant height.*—30–40 cm.
*Spreading area of plant* .—25–35 cm in diameter.
*Blooming period.*—April to September in the southern Kanto area, Japan.

Stem:
*Thickness.*—3.5–4.5 mm.
*Pubescence.*—Many.
*Branching.*—Abundant.
*Length of internode.*—2.0–3.0 cm.
*Color.*—Strong yellow green (R.H.S. 144B-144C, JHS 3512-3513)

Leaf:
*Shape.*—Elliptic.
*Length (average).* —3.5–5.0 cm.
*Width (average).*—3.0–4.5 cm.
*Color.*—Strong yellow green to moderate olive green (R.H.S. 144A-146 A. JHS 3507–3508).
*Phyllotaxis.*—Verticillate before blooming: opposite during blooming.
*Pubescence.*—Moderate.
*Thickness.*—0.5–0.7 mm.

Flower:
*Facing direction*—Opening obliquely upward.
*Type.*—Single.
*Shape.*—Funnel-shaped, with five-fissured limb.
*Waving of petal.*—Strong.
*Lobation of petal.*—Moderate.
*Diameter.*—8.0–9.0 cm.
*Color.*—Dark bluish purple (R.H.S. 86A, JHS 8308).
*Reproductive organs.*—1 normal pistil and 5 normal stamens
*Peduncle.*—2.0–2.5 mm in thickness, and 2.5–3.0 cm in length.
*Physiological and ecological characteristics.*—Moderate resistance to rain, heat, and disease and pest.

This new and distinct variety of petunia plant, "Revolution Violet No. 3", was asexually reproduced by cutting at the aforementioned the Plant Biotechnology Laboratory of SUNTORY Ltd., and the homogeneity and stability thereof were confirmed.

SUMMARY OF THE VARIETY

The new variety of petunia plant has a decumbent habit, long stems and vivid purple flower petal and thus is very different from a similar variety, "Falcon Blue". The plant has decumbent habit, over-abundant branching and great profusion blooms, and the whole bush remains in bloom for a considerable period of time. Especially primary branching is strong. The flowers are single and large, the petals having a vivid purple color, which is clearly distinguished from dark bluish purple of "Falcon Blue". The bottom color of the corolla throat is vivid purple and the outside of corolla tube is strong purple. The plant has a high resistance to rain, heat, drought and pest.

DESCRIPTION OF THE VARIETY

Figure 1:
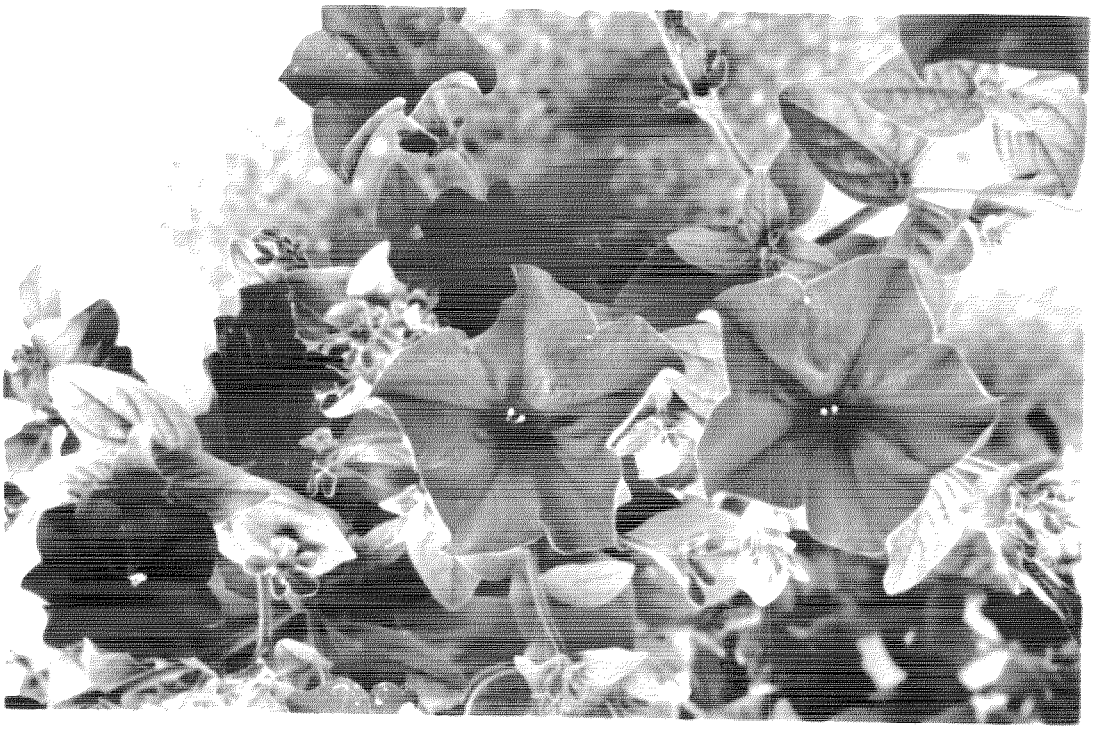
FIG. 1 is a photograph giving a partial view of the new variety of petunia plant planted in a flower pot.
Figure 2:
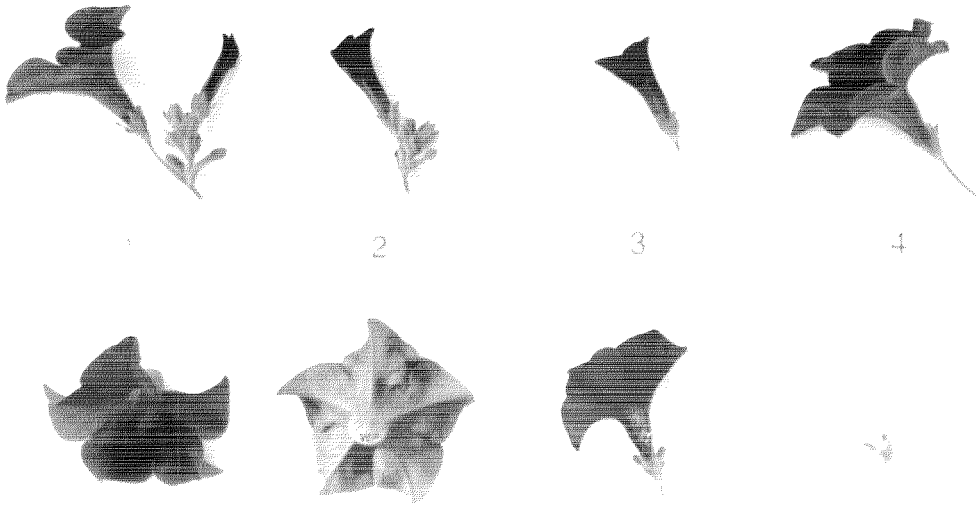
FIG. 2 is a photograph showing, in numerical order, a branch having an open flower(1), a current shoot(2), a bud(3), a side view of the flower(4), a front view of the flower(5), a rear view of the flower(6), an interior view of the flower(7), and pistil and stamen(8), of the new variety of petunia plant.

The botanical characteristics of the new and distinct variety of petunia plant "Revolution Violet No. 3" are as follows.

Plant:
*Growth habit.*—Decumbent. The stems hang down when potted in a hanging pot.
*Plant height.*—15–20 cm.
*Spreading area of plant.*—The stem extends to length of 50–60 cm from the base, and thus the spreading area of the plant is 60–100 cm in diameter.
*Growth.*—very vigorous with abundant branching, a great profusion of blooms; the whole bush remaining in bloom for a considerable this period of time.
*Blooming period.*—Late March to late September in the southern Kanto area, Japan. The plant shape does not change throughout this period.

Stem:

*Thickness.*—3.0–5.0 mm.

*Pubescence.*—Normal.

*Branching.*—Over-abundant. Particularly primary branching is strong.

*Length of internode.*—3.0–5.0 cm.

*Color.*—Deep yellow green to vivid yellow green (R.H.S. 144A , JHS 3507-3506).

Leaf:

*Shape.*—Oval.

*Length.*—3.0–5.0 cm.

*width.*—3.0–4.0 cm.

*Color.*—Dark yellow green to strong yellow green (R.H.S. 146A-145A, JHS 3508-3512).

*Thickness.*—0.5–0.7 mm.

*Phyllotaxis.*—Verticillate before blooming: opposite during blooming.

*Pubescence.*—Normal.

Flower:

*Facing direction.*—Opening obliquely upward.

*Type.*—Single.

*Shape.*—Funnel-shape, with five-fissured limb.

*Waving of petal.*—Week.

*Lobation of petal.*—Deep.

*Diameter.*—7.5–8.0 cm.

*Color.*—Vivid purple (R.H.S. 81A-82A, JHS 8606). Bottom color of the corolla throat is vivid purple (R.H.S 81B-82B, JHS 8605). The outside of corolla tube is strong purple (R.H.S. 83D, JHS 8612).

*Reproductive organs.*—1 normal pistil and 5 normal stamens. Both normal.

Physiological and ecological characteristics: High resistance to rain, heat, drought and pest.

This new variety of petunia plant is most suitable for flower bedding and potting, particularly in hanging pots or planters, and is further excellent for ground cover.

The plant of this new variety "Revolution Violet No. 3" is presently planted and maintained at the Plant Biotechnology Laboratory of SUNTORY Ltd., residing at 863-1, Aza-Iketani, Oomori-cho, Youkaiti-shi, Shiga-ken, Japan.

I Claim:

1. A new and distinct variety of petunia plant, substantially as herein illustrated and described, characterized particularly as to novelty by (A) being a decumbent habit plant having long stems, (B) an over-abundant branching, Particularly primary branching is strong, and great profusion blooms, the whole bush remaining in bloom for a considerable period of time, (C) flowers are single and large, the petals having a vivid purple color, and the bottom color of the corolla throat is vivid purple and the outside of corolla tube is strong purple (D) a high resistance to rain, heat, drought and pests.

* * * * *